United States Patent
Zhang et al.

(10) Patent No.: US 8,859,594 B2
(45) Date of Patent: Oct. 14, 2014

(54) POLYMORPHS OF N-(6-(4-CHLOROPHENOXY)HEXYL)-N'-CYANO-N''-(4-PYRIDYL)GUANIDINE, AND PREPARATION THEREOF AND USE THEREOF

(75) Inventors: Hesheng Zhang, Tianjin (CN); Xin Chen, Tianjin (CN)

(73) Assignees: Tianjin Hemay Bio-Tech Co., Ltd., Tianjin (CN); Tianjin Michele Sci-Tech Development Co., Ltd., Tianjin (CN)

( * ) Notice: Subject to any disclaimer, the term of this patent is extended or adjusted under 35 U.S.C. 154(b) by 0 days.

(21) Appl. No.: 13/881,706

(22) PCT Filed: Oct. 25, 2011

(86) PCT No.: PCT/CN2011/081238
§ 371 (c)(1),
(2), (4) Date: Jul. 12, 2013

(87) PCT Pub. No.: WO2012/055346
PCT Pub. Date: May 3, 2012

(65) Prior Publication Data
US 2013/0281494 A1    Oct. 24, 2013

(30) Foreign Application Priority Data

Oct. 26, 2010  (CN) .......................... 2010 1 0519331

(51) Int. Cl.
C07D 213/75 (2006.01)
C07D 213/74 (2006.01)
A61K 31/4409 (2006.01)
A61P 35/00 (2006.01)

(52) U.S. Cl.
CPC .................................. C07D 213/75 (2013.01)

USPC .......... 514/352; 514/353; 546/304; 546/306; 546/312

(58) Field of Classification Search
USPC .......................................... 514/352; 546/312
See application file for complete search history.

(56) References Cited

U.S. PATENT DOCUMENTS 5,696,140 A    12/1997   Bramm et al.
2012/0029036 A1*  2/2012  Zhang et al. .................. 514/352

FOREIGN PATENT DOCUMENTS

WO   WO 2010/088842   *  8/2010

OTHER PUBLICATIONS

Chern et al.; "Synthesis and in vitro cytotoxicity of 5-substituted 2-cyanoimino-4-imidazodinone and 2-cyanoimino-4-pyrimidinone derivatives"; *Bioorganic & Medicinal Chemistry Letters*; 14:1169-1172 (2004).
Schou et al.; "Novel cyanoguanidines with potent oral antitumor activity"; *Bioorganic & Medicinal Chemistry Letters*; 7(24):3095-3100 (1997).
The International Search Report from PCT/CN2011/081238, dated Feb. 9, 2012 *English Translation* version.

* cited by examiner

*Primary Examiner* — John Mabry
*Assistant Examiner* — Daniel Carcanague
(74) *Attorney, Agent, or Firm* — Kilpatrick Townsend & Stockon LLP

(57) ABSTRACT

Disclosed are a polymorphs I-VI of N-(6-(4-chlorophenoxy)hexyl)-N'-cyano-N''-(4-pyridyl)guanidine or of a solvate thereof, a preparation method thereof, and a use thereof as a biological active ingredient. The polymorphs are useful in treatment of cancers, and diseases or disorders caused by abnormal cell proliferation.

3 Claims, 3 Drawing Sheets

X-ray Powder Diffraction of Polymorph 1 of N-(6-(4-chlorophenoxy)hexyl)-N'-cyano-N''-(4-pyridyl)guanidine

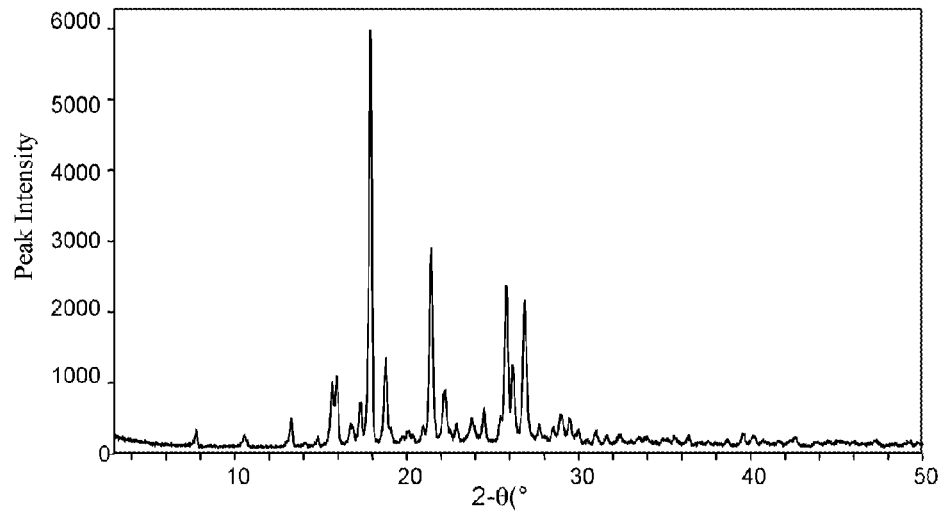
FIG. 1: X-ray Powder Diffraction of Polymorph I of N-(6-(4-chlorophenoxy)hexyl)-N'-cyano-N''-(4-pyridyl)guanidine
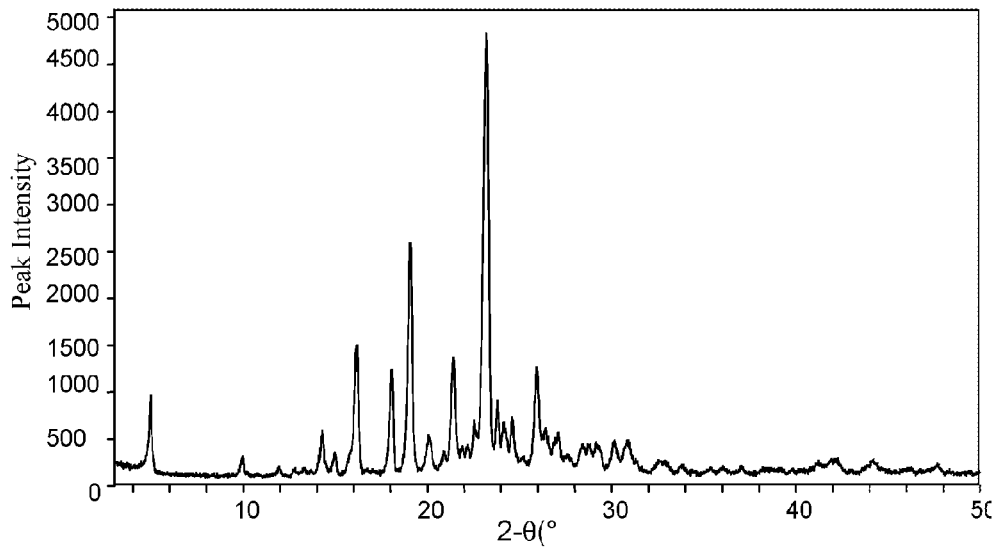
FIG. 2: X-ray Powder Diffraction of Polymorph II of N-(6-(4-chlorophenoxy)hexyl)-N'-cyano-N''-(4-pyridyl)guanidine

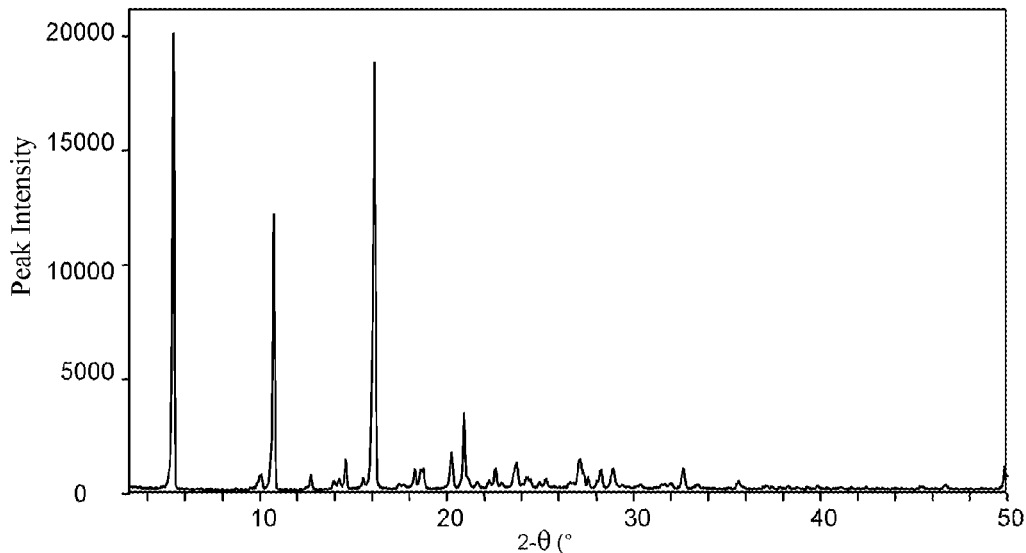
FIG. 3: X-ray Powder Diffraction of Polymorph III of N-(6-(4-chlorophenoxy)hexyl)-N'-cyano-N''-(4-pyridyl)guanidine
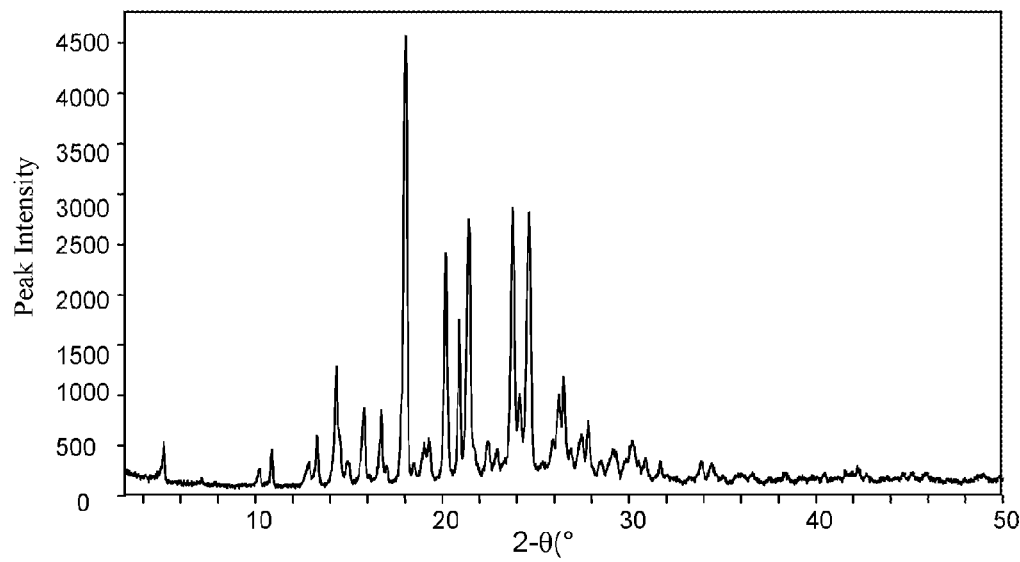
FIG. 4: X-ray Powder Diffraction of Polymorph IV of N-(6-(4-chlorophenoxy)hexyl)-N'-cyano-N''-(4-pyridyl)guanidine

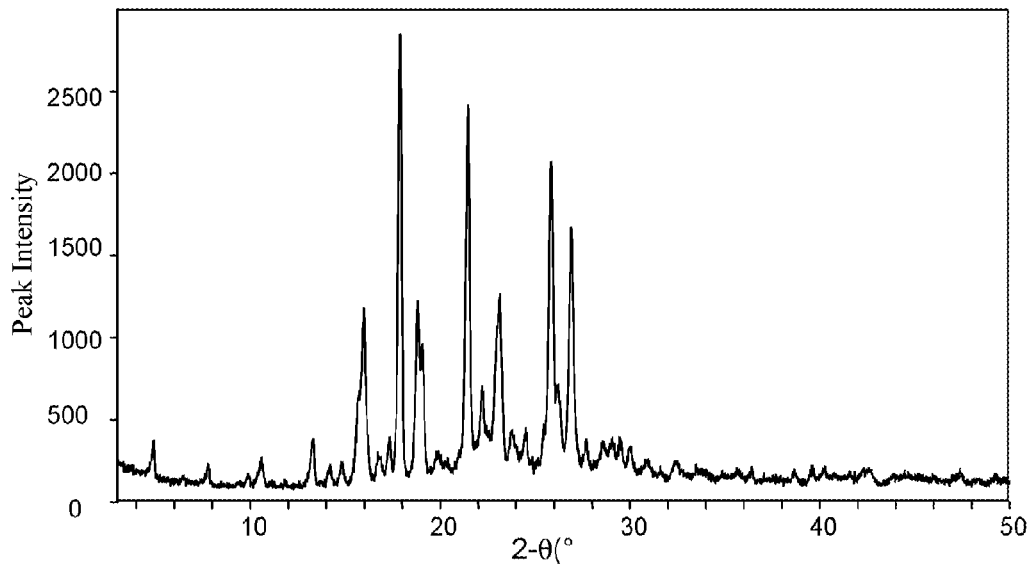
FIG. 5: X-ray Powder Diffraction of Polymorph V of N-(6-(4-chlorophenoxy)hexyl)-N'-cyano-N''-(4-pyridyl)guanidine
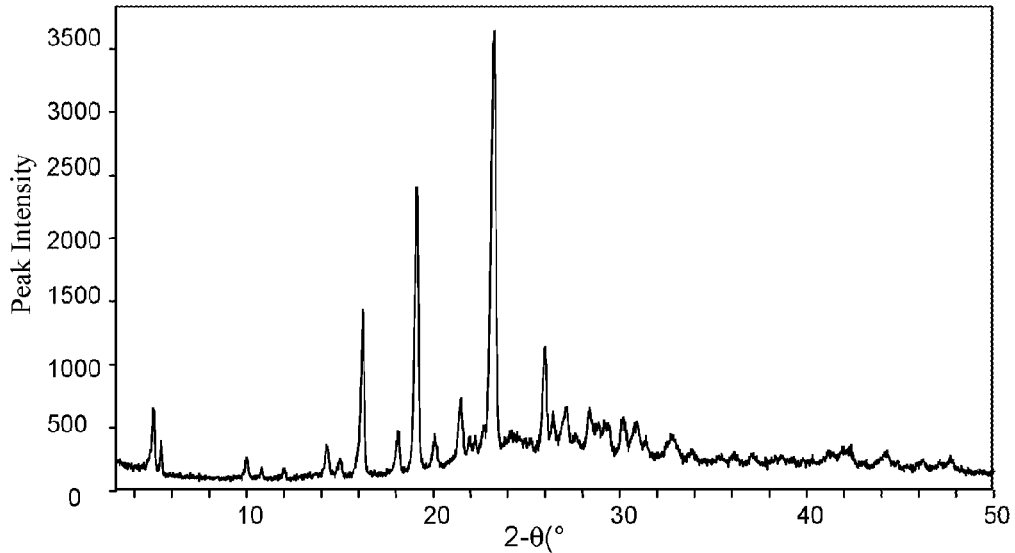
FIG. 6: X-ray Powder Diffraction of Polymorph VI of N-(6-(4-chlorophenoxy)hexyl)-N'-cyano-N''-(4-pyridyl)guanidine

POLYMORPHS OF N-(6-(4-CHLOROPHENOXY)HEXYL)-N'-CYANO-N"-(4-PYRIDYL)GUANIDINE, AND PREPARATION THEREOF AND USE THEREOF

CROSS-REFERENCE TO RELATED APPLICATIONS

This application is the U.S. National Stage entry of PCT/CN2011/081238, filed Oct. 25, 2011, which claims benefit of China Patent Application No. 201010519331.8, filed Oct. 26, 2010, the disclosures of each are herein incorporated by reference.

FIELD OF THE INVENTION

The present invention relates to polymorphs of N-(6-(4-chlorophenoxy)hexyl)-N'-cyano-N"-(4-pyridyl)guanidine, preparation methods and uses thereof.

BACKGROUND OF THE INVENTION

It was initially found that pyridyl cyanoguanidines such as pinacidil (N-1,2,2-trimethylpropyl-N'-cyano-N"-(4-pyridyl)guanidine) are potassium-channel openers and therefore they were developed as antihypertensive agents. If the side chain of pinacidil was replaced with longer aryl group-containing side chain, it will lose its antihypertensive activity. However, in another aspect, it was found that the resulting compound has an antitumor activity when it is administered orally in a rat model with Yoshida ascitic tumor.

Various kinds of pyridyl cyanoguanidines with antiproliferative activities are disclosed in such as EP 660823, WO 98/54141, WO 98/54143, WO 98/54144, WO 98/54145, WO 00/61559 and WO 00/61561, WO 98/54146, WO 2002/094813, U.S. Pat. No. 5,696,140. The structure-activity relation (SAR) of such compounds is discussed in C. Schou et al., *Bioorganic and Medicinal Chemistry Letters* 7 (24), 1997, 3095-3100, in which the antiproliferative effects of a large number of pyridyl cyanoguanidines on various human lung cancer and breast cancer cell lines as well as normal human fibroblasts have been tested in vitro. The compounds have been also tested in vivo by using nude mice with human lung cancer tumor xenograft. A specific compound (N-(6-(4-chlorophenoxy)hexyl)-N'-cyano-N"-(4-pyridyl)guanidine) with high antiproliferative activity in vitro and potent antitumor activity in the nude mice model was selected according to the SAR analysis.

Test results of further in vitro and in vivo tests of the compound N-(6-(4-chlorophenoxy)hexyl)-N'-cyano-N"-(4-pyridyl)guanidine are reported in P-J V Hjarnaa et al., *Cancer Res.* 59, 1999, 5751-5757. The compound exhibits an efficacy comparable to those of cytostatic agents daunorubicin and paclitaxel as control compounds in vitro, and also shows significantly lower antiproliferative activity against normal human endothelial cells. In the in vivo test carried out with nude mouse transplanted with human tumor cells, this compound shows highly potent antitumor activity and can also inhibit tumor cells which were resistant to conventional antitumor drugs such as paclitaxel.

It is well known that a crystalline form of a compound has a better stability than an amorphous form thereof, which can extend a shelf life of a drug substance, and is more suitable for preparing a formulation. As a result, a crystalline form, for example, a polymorph is a best choice of a physical form of a drug substance. However, no polymorph of N-(6-(4-chlorophenoxy)hexyl)-N'-cyano-N"-(4-pyridyl)guanidine (i.e. a compound of Formula (I)) is reported up to now.

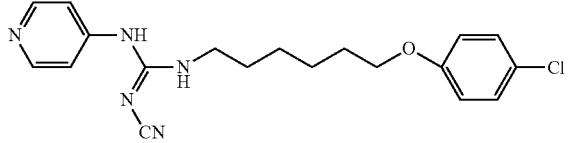

Formula (I)

SUMMARY OF THE INVENTION

One object of the present invention is to provide polymorphs of N-(6-(4-chlorophenoxy)hexyl)-N'-cyano-N"-(4-pyridyl)guanidine or polymorphs of solvates thereof.

Another object of the present invention is to provide methods for preparing polymorphs of N-(6-(4-chlorophenoxy)hexyl)-N'-cyano-N"-(4-pyridyl)guanidine or polymorphs of solvates thereof and uses thereof.

The polymorphs of N-(6-(4-chlorophenoxy)hexyl)-N'-cyano-N"-(4-pyridyl)guanidine or the polymorphs of the solvates thereof according to the present invention can be prepared by one of the following methods.

1. N-(6-(4-chlorophenoxy)hexyl)-N'-cyano-N"-(4-pyridyl)guanidine is added to a single solvent and dissolved therein by heating, and the resulting clear solution is stood and cooled to room temperature or to below room temperature to precipitate a solid.

2. N-(6-(4-chlorophenoxy)hexyl)-N'-cyano-N"-(4-pyridyl)guanidine is added to a mixed solvent and dissolved therein by heating, and the resulting clear solution is stood and cooled to room temperature or to below room temperature to precipitate a solid.

3. N-(6-(4-chlorophenoxy)hexyl)-N'-cyano-N"-(4-pyridyl)guanidine is added to a single solvent and dissolved therein by heating, and the resulting clear solution is cooled to room temperature or to below room temperature under stirring to precipitate a solid.

4. N-(6-(4-chlorophenoxy)hexyl)-N'-cyano-N"-(4-pyridyl)guanidine is added to a single solvent and dissolved therein by heating, and then to the resulting clear solution a poor solvent is added dropwise under stirring, and meanwhile the resulting mixture is cooled to room temperature or to below room temperature to precipitate a solid.

5. N-(6-(4-chlorophenoxy)hexyl)-N'-cyano-N"-(4-pyridyl)guanidine is added to a mixed solvent and dissolved therein by heating, and the resulting clear solution is cooled to room temperature or to below room temperature under stirring to precipitate a solid.

6. N-(6-(4-chlorophenoxy)hexyl)-N'-cyano-N"-(4-pyridyl)guanidine is added to a mixed solvent and dissolved therein by heating, and the resulting clear solution is cooled to room temperature or to below room temperature under stirring, and meanwhile a poor solvent is added dropwise to precipitate a solid.

7. N-(6-(4-chlorophenoxy)hexyl)-N'-cyano-N"-(4-pyridyl)guanidine is added to a single solvent or a mixed solvent; the resulting mixture is refluxed but does not form a clear solution; and then the resulting mixture is refluxed or stirred, and cooled to room temperature or to below room temperature.

8. N-(6-(4-chlorophenoxy)hexyl)-N'-cyano-N"-(4-pyridyl)guanidine is added to a two-phase system formed from an acidic aqueous solution and an organic solvent, and the resulting mixture is adjusted to pH>7 with a basic solution to precipitate a solid.

The term "single solvent" used herein refers to any solvent selected from the group consisting of water, alcohols, esters, ketones, ethers, amides, sulphones, alkanes, halogenated alkanes, pyridines, nitriles, aromatic hydrocarbons, cyclic ethers and sulphoxides, including but not limited to any one of methanol, ethanol, propanol, isopropanol, ethylene glycol, propylene glycol, acetone, butanone, diethyl ether, isopropyl ether, tetrahydrofuran, 1,4-dioxane, ethyl formate, ethyl acetate, propyl formate, isopropyl formate, methyl acetate, propyl acetate, isopropyl acetate, butyl formate, N,N-dimethylformamide, N,N-dimethylacetamide, dimethyl sulphoxide, water, pyridine, acetonitrile, benzene, toluene, xylol, ethylene glycol dimethyl ether, ethylene glycol monomethyl ether, ethylene glycol diethyl ether, ethylene glycol monoethyl ether, ethylene glycol dipropyl ether, ethylene glycol monopropyl ether, n-hexane, chloroform, dichloromethane, 1,2-dichloroethane, triethylamine, trimethylamine, pyridine, N-methylmorpholine, N-methylpyrrolidine, acetonitrile, water, petroleum ether and carbon tetrachloride.

The term "mixed solvent" used herein refers to a mixed solution of two or more solvents selected from the group consisting of water, alcohols, esters, ketones, ethers, amides, sulphones, alkanes, halogenated alkanes, pyridines, nitriles, aromatic hydrocarbons, cyclic ethers and sulphoxides, specifically including but not limited to a mixed solution of two or more solvents selected from the group consisting of methanol, ethanol, propanol, isopropanol, ethylene glycol, propylene glycol, acetone, butanone, diethyl ether, isopropyl ether, tetrahydrofuran, 1,4-dioxane, ethyl formate, ethyl acetate, propyl formate, isopropyl formate, methyl acetate, propyl acetate, isopropyl acetate, butyl formate, N,N-dimethylformamide, N,N-dimethylacetamide, dimethyl sulphoxide, water, pyridine, acetonitrile, benzene, toluene, xylol, ethylene glycol dimethyl ether, ethylene glycol monomethyl ether, ethylene glycol diethyl ether, ethylene glycol monoethyl ether, ethylene glycol dipropyl ether, ethylene glycol monopropyl ether, n-hexane, chloroform, dichloromethane, 1,2-dichloroethane, carbon tetrachloride, triethylamine, trimethylamine, pyridine, N-methylmorpholine, N-methylpyrrolidine, acetonitrile, water and petroleum ether. If the mixed solvent is a mixture of above-mentioned two solvents, a ratio of the two solvents is in the range of from 100:1 to 1:100.

The term "poor solvent" used herein refers to one or more solvents selected from the group consisting of water, alcohols, esters, ketones, ethers, amides, sulphones, alkanes, halogenated alkanes, pyridines, nitriles, aromatic hydrocarbons, cyclic ethers and sulphoxides, including but not limited to one or more solvents selected from the group consisting of methanol, ethanol, propanol, isopropanol, ethylene glycol, propylene glycol, acetone, butanone, diethyl ether, isopropyl ether, tetrahydrofuran, 1,4-dioxane, ethyl formate, ethyl acetate, propyl formate, isopropyl formate, methyl acetate, propyl acetate, isopropyl acetate, butyl formate, water, pyridine, acetonitrile, benzene, toluene, xylol, ethylene glycol dimethyl ether, ethylene glycol monomethyl ether, ethylene glycol diethyl ether, ethylene glycol monoethyl ether, ethylene glycol dipropyl ether, ethylene glycol monopropyl ether, n-hexane, chloroform, dichloromethane, carbon tetrachloride, 1,2-dichloroethane, triethylamine, trimethylamine, pyridine, N-methylmorpholine, N-methylpyrrolidine, acetonitrile, water and petroleum ether. If the poor solvent is a mixture of above-mentioned two solvents, a ratio of the two solvents is in the range of from 100:1 to 1:100.

The term "acidic aqueous solution" used herein refers to any one or more of hydrochloric acid aqueous solution, sulfuric acid aqueous solution, phosphoric acid aqueous solution, nitric acid aqueous solution, citric acid aqueous solution, acetic acid aqueous solution, formic acid aqueous solution, malonic acid aqueous solution, methanesulfonic acid aqueous solution, benzenesulfonic acid aqueous solution and p-toluenesulfonic acid aqueous solution.

The term "basic aqueous solution" used herein refers to any one or more of sodium hydroxide aqueous solution, potassium hydroxide aqueous solution, sodium carbonate aqueous solution, potassium carbonate aqueous solution, sodium bicarbonate aqueous solution, potassium bicarbonate aqueous solution, aqueous ammonia, methylamine aqueous solution, dimethylamine aqueous solution, trimethylamine aqueous solution, ethylamine aqueous solution, diethylamine aqueous solution, triethylamine aqueous solution, morpholine aqueous solution, N-methyl morpholine aqueous solution, N-ethyl morpholine aqueous solution, N-propyl morpholine aqueous solution, piperidine aqueous solution, N-methyl piperidine aqueous solution, N-ethyl piperidine aqueous solution, pyrrolidine aqueous solution, N-methylpyrrolidine aqueous solution and N-ethyl pyrrolidine aqueous solution.

The present invention discloses six polymorphs of N-(6-(4-chlorophenoxy)hexyl)-N'-cyano-N"-(4-pyridyl)guanidine, i.e. polymorphs I to VI.

In the present invention, X-ray Powder Diffraction is performed under the following measurement conditions.

| | |
|---|---|
| Sample Weight: | about 100 mg |
| Target: | Cu |
| Filter Disk: | monochromatic filter |
| Voltage/Current: | 40 kV/100 mA |
| Slit: | SS/DS 1°, RS 0.3 mm |
| Scanning Rate: | 8°/min |
| Range: | 3-50 |

Peaks with peak intensity equal or greater than 15 in X-ray powder diffraction patterns of the six polymorphs of N-(6-(4-chlorophenoxy)hexyl)-N'-cyano-N"-(4-pyridyl)guanidine according to the present invention are shown in the following tables.

(1) Polymorph I of N-(6-(4-chlorophenoxy)hexyl)-N'-cyano-N"-(4-pyridyl)guanidine Peaks in X-ray powder diffraction pattern thereof have the following features:

| Diffraction Angle ($2\theta$, °) | Intensity ($I/I_0$) | Diffraction Angle ($2\theta$, °) | Intensity ($I/I_0$) |
|---|---|---|---|
| 15.679 | 15.3 | 15.940 | 16.5 |
| 17.901 | 100 | 18.779 | 20.4 |
| 21.439 | 46.4 | 25.781 | 36.6 |
| 26.162 | 16.6 | 26.861 | 32.5 |

(2) Polymorph II of N-(6-(4-chlorophenoxy)hexyl)-N'-cyano-N"-(4-pyridyl)guanidine Peaks in X-ray powder diffraction pattern thereof have the following features:

| Diffraction Angle ($2\theta$, °) | Intensity ($I/I_0$) | Diffraction Angle ($2\theta$, °) | Intensity ($I/I_0$) |
|---|---|---|---|
| 4.978 | 18.0 | 16.199 | 30.3 |
| 18.080 | 24.3 | 19.061 | 54.5 |

-continued

| Diffraction Angle (2θ, °) | Intensity (I/I₀) | Diffraction Angle (2θ, °) | Intensity (I/I₀) |
|---|---|---|---|
| 21.401 | 24.1 | 23.219 | 100.0 |
| 25.939 | 22.0 | | |

(3) Polymorph III of N-(6-(4-chlorophenoxy)hexyl)-N'-cyano-N''-(4-pyridyl)guanidine Peaks in X-ray powder diffraction pattern thereof have the following features:

| Diffraction Angle (2θ, °) | Intensity (I/I₀) | Diffraction Angle (2θ, °) | Intensity (I/I₀) |
|---|---|---|---|
| 5.378 | 100 | 10.741 | 60.3 |
| 16.140 | 93.5 | 20.939 | 16.4 |

(4) Polymorph IV of N-(6-(4-chlorophenoxy)hexyl)-N'-cyano-N''-(4-pyridyl)guanidine Peaks in X-ray powder diffraction pattern thereof have the following features:

| Diffraction Angle (2θ, °) | Intensity (I/I₀) | Diffraction Angle (2θ, °) | Intensity (I/I₀) |
|---|---|---|---|
| 14.340 | 26.5 | 15.821 | 16.3 |
| 16.759 | 15.9 | 18.040 | 100.0 |
| 20.201 | 50.1 | 20.921 | 34.3 |
| 21.421 | 57.3 | 23.781 | 58.7 |
| 24.139 | 16.6 | 24.660 | 57.9 |
| 26.260 | 16.1 | 26.484 | 20.2 |

(5) Polymorph V of N-(6-(4-chlorophenoxy)hexyl)-N'-cyano-N''-(4-pyridyl)

Peaks in X-ray powder diffraction pattern thereof have the following features:

| Diffraction Angle (2θ, °) | Intensity (I/I₀) | Diffraction Angle (2θ, °) | Intensity (I/I₀) |
|---|---|---|---|
| 15.701 | 19.3 | 15.999 | 39.2 |
| 17.901 | 100 | 18.839 | 38.9 |
| 21.479 | 79.3 | 23.159 | 34.2 |
| 25.841 | 66.8 | 26.219 | 15.2 |
| 26.920 | 51.2 | | |

(6) Polymorph VI of N-(6-(4-chlorophenoxy)hexyl)-N'-cyano-N''-(4-pyridyl)guanidine Peaks in X-ray powder diffraction pattern thereof have the following features:

| Diffraction Angle (2θ, °) | Intensity (I/I₀) | Diffraction Angle (2θ, °) | Intensity (I/I₀) |
|---|---|---|---|
| 5.023 | 15.2 | 16.240 | 39.5 |
| 19.121 | 67.6 | 23.260 | 100 |
| 25.979 | 23.5 | | |

The polymorphs of N-(6-(4-chlorophenoxy)hexyl)-N'-cyano-N''-(4-pyridyl)guanidine according to the present invention may be in a form of an individual polymorph or a mixture of two or more polymorphs when in use.

The polymorphs of N-(6-(4-chlorophenoxy)hexyl)-N'-cyano-N''-(4-pyridyl)guanidine or the polymorphs of the solvates thereof according to the present invention can be formulated into a drug for treating proliferative diseases, including but not limit to various cancers, and diseases or disorders caused by abnormal cell proliferation. More specifically, the proliferative diseases include but not limited to leukemia, acute granulocytic leukemia, chronic granulocytic leukemia, chronic lymphocytic leukemia, myelodysplasia, multiple myeloma, Hodgkin's disease and non-hodgkin's lymphoma, small cell lung cancer and non-small cell lung cancer, gastric cancer, intestinal cancer, colon cancer, rectal cancer, prostate cancer, ovarian cancer, breast cancer, cerebral cancer, head and neck cancer, urethral cancer, renal cancer, urinary bladder cancer, melanoma, liver cancer, skin cancer, uterine cancer and pancreatic cancer.

The polymorphs of N-(6-(4-chlorophenoxy)hexyl)-N'-cyano-N''-(4-pyridyl)guanidine or the polymorphs of the solvates thereof according to the present invention can be also used in combination with one or more of other compounds for treating proliferative diseases. When the polymorphs according to the present invention are combined with other compounds, they can be used simultaneously or sequentially. Other compounds for treating proliferative diseases, which can be used in combination with the polymorphs of N-(6-(4-chlorophenoxy)hexyl)-N'-cyano-N''-(4-pyridyl)guanidine or the polymorphs of the solvates thereof according to the present invention, include but not limited to triazine derivatives such as hexamethylmelamine; enzymes such as asparagine enzyme; antibacterial agents such as bleomycin, dactinomycin, daunorubicin, adriamycin, idarubicin, mitomycin, epirubicin or plicamycin; alkylating agents such as busulfan, carboplatin, carmustine, chlorambucil, cisplatin, cyclophosphamide, dacarbazine, isocyclophosphamide, lomustine, chlormethine, melphalan, procarbazine or thiotepa; antimetabolic agents such as cladribine, cytarabine, floxuridine, fludarabine, fluorouracil, hydroxyurea, mercaptopurine, methotrexate, gemcitabine, pentostatin or thioguanine; antimitotic agents such as etoposide, paclitaxel, teniposide, vinblastine, vinorelbine or vincristine; hormone drugs such as aromatic enzyme inhibitors e.g. aminoglutethimide; corticosteroids such as dexamethasone, prednison or luteinizing hormone releasing hormone (LH-RH); antiestrogenic agents such as tamoxifen, formestane or letrozole; antiandrogen agents such as flutamide; biological response modifiers such as aldesleukin in lymphokine or other interleukins; interferons such as interferon-α; growth factors such as erythropoietin, filgrastim or sargramostim; differentiation agents such as vitamin D derivatives e.g seocalcitol; all-trans retinoic acid; immunomodulators such as levamisol; monoclonal antibody; tumor necrosis factor α; or angiogenesis inhibitors. Other compounds for treating the proliferative diseases, which are more suitable to be used in combination with the polymorphs of N-(6-(4-chlorophenoxy)hexyl)-N'-cyano-N''-(4-pyridyl) guanidine or the polymorphs of the solvates thereof according to the present invention, are one or more selected from the group consisting of paclitaxel, fluorouracil, etoposide, cyclophosphamide, cis-platinum, carboplatin, vincristine, gemcitabine, vinorelbine, chlorambucil, adriamycin, phenylalanine mustard and seocalcitol.

When the polymorphs of N-(6-(4-chlorophenoxy)hexyl)-N'-cyano-N''-(4-pyridyl)guanidine or the polymorphs of the solvates thereof according to the present invention are used to treat the proliferative diseases, they can be also used in combination with ionizing radiation.

When the polymorphs of N-(6-(4-chlorophenoxy)hexyl)-N'-cyano-N''-(4-pyridyl)guanidine or the polymorphs of the solvates thereof according to the present invention are used to treat the proliferative diseases, they can be also used in combination with an agent for alleviating side effects of antitumor therapy. The agent for alleviating side effects of antitumor therapy includes but not limited to amifostine, folinic acid and mesna.

The present invention further relates to pharmaceutical formulations comprising the polymorphs of N-(6-(4-chlorophenoxy)hexyl)-N'-cyano-N"-(4-pyridyl)guanidine or the polymorphs of the solvates thereof. The formulations according to the present invention refer to appropriate pharmaceutical dosage forms prepared from the polymorphs of N-(6-(4-chlorophenoxy)hexyl)-N'-cyano-N"-(4-pyridyl)guanidine or the polymorphs of the solvates thereof alone or along with necessary pharmaceutically acceptable pharmaceutical excipients such that they are suitable to be used via various administration routes, including but not limited to oral administration, buccal administration, intravenous injection, intraperitoneal injection, subcutaneous injection, intramuscular injection, nasal drop, eye drop, inhalation, rectal administration, vaginal administration, epidermal administration and the like. The appropriate pharmaceutical dosage forms include but not limited to infusions, conventional solutions for injection, powders for injection, lyophilized powders for injection, oral solutions, syrups, tablets, pills, capsules, granules, gels, soft capsules, suppositories, aerosols and creams. The polymorphs of N-(6-(4-chlorophenoxy)hexyl)-N'-cyano-N"-(4-pyridyl)guanidine or the polymorphs of the solvates thereof are 0.1-100% by weight of the pharmaceutical formulations. A unit dosage comprises 0.01 mg to 500 mg of the polymorphs of N-(6-(4-chlorophenoxy)hexyl)-N'-cyano-N"-(4-pyridyl)guanidine or the polymorphs of the solvates thereof, and more preferable unit dosage comprises 0.1 mg to 500 mg of the polymorphs of N-(6-(4-chlorophenoxy)hexyl)-N'-cyano-N"-(4-pyridyl)guanidine or the polymorphs of the solvates thereof. The term "unit dosage" refers to a unit which can be administered to a patient and easily operated and packed, i.e. a single dosage.

When the polymorphs of N-(6-(4-chlorophenoxy)hexyl)-N'-cyano-N"-(4-pyridyl)guanidine or the polymorphs of the solvates thereof according to the present invention are formulated into lyophilized powders for injection, a pharmaceutically acceptable lyophilizing excipient may be or not be further added. The pharmaceutically acceptable lyophilizing excipient is one or more selected from the group consisting of α-cyclodextrin, β-cyclodextrin, γ-cyclodextrin, hydroxypropyl-β-cyclodextrin, sulfobutylether-β-cyclodextrin, mannitol, sorbitol, sodium chloride, glucose, fructose, sucrose, dextran, xylitol and lactose.

When the polymorphs of N-(6-(4-chlorophenoxy)hexyl)-N'-cyano-N"-(4-pyridyl)guanidine according to the present invention are formulated into conventional powders for injection, conventional solutions for injection or lyophilized powders for injection, an appropriate amount of pharmaceutically acceptable sterile diluent can be added prior to use so as to prepare a solution formulation for intramuscular injection or intravenous administration. The pharmaceutically acceptable sterile diluent includes but not limited to water for injection, physiological saline, glucose water, and other known aqueous carriers.

BRIEF DESCRIPTIONS OF THE DRAWINGS

FIG. 1 is X-ray powder diffraction pattern of the polymorph I of N-(6-(4-chlorophenoxy)hexyl)-N'-cyano-N"-(4-pyridyl)guanidine.

FIG. 2 is X-ray powder diffraction pattern of the polymorph II of N-(6-(4-chlorophenoxy)hexyl)-N'-cyano-N"-(4-pyridyl)guanidine.

FIG. 3 is X-ray powder diffraction pattern of the polymorph III of N-(6-(4-chlorophenoxy)hexyl)-N'-cyano-N"-(4-pyridyl)guanidine.

FIG. 4 is X-ray powder diffraction pattern of the polymorph IV of N-(6-(4-chlorophenoxy)hexyl)-N'-cyano-N"-(4-pyridyl)guanidine.

FIG. 5 is X-ray powder diffraction pattern of the polymorph V of N-(6-(4-chlorophenoxy)hexyl)-N'-cyano-N"-(4-pyridyl)guanidine.

FIG. 6 is X-ray powder diffraction pattern of the polymorph VI of N-(6-(4-chlorophenoxy)hexyl)-N'-cyano-N"-(4-pyridyl)guanidine.

DETAILED DESCRIPTION OF THE INVENTION

The melting point detector used herein is BUCHI-B-545; and the melting point tube used herein is 0.9-1.1 mm melting point tube produced by Instrument Factory of West China University of Medical Sciences.

Example 1

Polymorph I

Method a: To a mixture of 10 mL of THF (tetrahydrofuran) and 0.5 mL of TEA (triethylamine) 0.5 g of N-(6-(4-chlorophenoxy)hexyl)-N'-cyano-N"-(4-pyridyl)guanidine was added. The resulting mixture was heated to 85° C. and refluxed to obtain a clear solution. The resulting clear solution was stood and cooled to room temperature, then moved into a refrigerator at −20° C. and frozen overnight. A crystal was precipitated, and filtered under suction. The cake was dried in air to obtain the polymorph I. Melting Point: 151-153° C.

Method b: 0.5 g of N-(6-(4-chlorophenoxy)hexyl)-N'-cyano-N"-(4-pyridyl)guanidine was added to 10 mL of ACN (acetonitrile). The resulting mixture was heated to 85° C. to obtain a clear solution. The resulting clear solution was stood and cooled to room temperature, then moved into a refrigerator at 5° C. and refrigerated overnight. A crystal was precipitated, and filtered under suction. The cake was dried in air to obtain the polymorph I.

Method c: 0.5 g of the polymorph VI of N-(6-(4-chlorophenoxy)hexyl)-N'-cyano-N"-(4-pyridyl)guanidine was added to 8 mL of acetone. The resulting mixture was heated to reflux, further refluxed for 20 min, and did not form a clear solution. The resulting mixture was stood and cooled to room temperature, and then filtered under suction. The cake was dried in air to obtain the polymorph I.

Method d: 0.5 g of the polymorph VI of N-(6-(4-chlorophenoxy)hexyl)-N'-cyano-N"-(4-pyridyl)guanidine was added to 5 mL of diethyl ether. The resulting mixture was heated to 40° C. and stirred for 1 h, then cooled to room temperature and stirred for additional 1 h, and filtered under suction. The cake was dried in air to obtain the polymorph I.

Method e: 0.5 g of N-(6-(4-chlorophenoxy)hexyl)-N'-cyano-N"-(4-pyridyl)guanidine was added to 10 mL of absolute ethanol. The resulting mixture was heated to 85° C. to obtain a clear solution. The resulting clear solution was cooled to room temperature under stirring, then moved into a refrigerator at −20° C. and cooled for 0.5 h, and filtered under suction. The cake was dried in air to obtain the polymorph I.

Method f: To a mixture of 2 mL of DMA (N,N-dimethylacetamide) and 10 mL of DCM (dichloromethane) 0.5 g of N-(6-(4-chlorophenoxy)hexyl)-N'-cyano-N"-(4-pyridyl)guanidine was added. The resulting mixture was heated to 60° C. and refluxed for 0.5 h to obtain a clear solution. The resulting clear solution was stood and cooled to room temperature, and then filtered under suction. The cake was dried in air to obtain the polymorph I.

The X-ray powder diffraction pattern of the polymorph I was shown in FIG. 1.

Example 2

Polymorph II

Method a: 0.5 g of the polymorph VI of N-(6-(4-chlorophenoxy)hexyl)-N'-cyano-N"-(4-pyridyl)guanidine was added to 30 mL of ethanol. The resulting mixture was heated to 85° C. and refluxed for 10 min, and a small amount of insoluble substance was removed by filtration while the mixture was still hot. The resulting colorless clear solution was concentrated to 5 mL, stood and cooled to room temperature, kept for 3 h, and then filtered under suction. The cake was dried in air to obtain the polymorph II. Melting Point: 149-151° C.

Method b: To a mixture of 3 mL of ethylene glycol monomethyl ether and 1 mL of water 0.5 g of N-(6-(4-chlorophenoxy)hexyl)-N'-cyano-N"-(4-pyridyl)guanidine was added. The resulting mixture was heated to 95° C. to obtain a clear solution. The resulting clear solution was stood and cooled to room temperature. A crystal was precipitated, and filtered under suction. The cake was dried in air to obtain the polymorph II.

Method c: To a mixture of 5 mL of methanol and 1.5 mL of water 0.5 g of N-(6-(4-chlorophenoxy)hexyl)-N'-cyano-N"-(4-pyridyl)guanidine was added. The resulting mixture is heated to 80° C. to obtain a clear solution. The resulting clear solution was stood and cooled to room temperature. A crystal was precipitated, and filtered under suction. The cake was dried in air to obtain the polymorph II.

Method d: 2 g of N-(6-(4-chlorophenoxy)hexyl)-N'-cyano-N"-(4-pyridyl)guanidine was added to 50 mL of 0.1 N hydrochloric acid aqueous solution to obtain a clear solution, and thereto 50 mL of ethyl acetate was added. The resulting mixture was adjusted to pH 10 with 10% KOH aqueous solution under stirring. A large amount of crystal was precipitated, and filtered under suction. The cake was dried in air to obtain the polymorph II.

The X-ray powder diffraction pattern of the polymorph II was shown in FIG. 2.

Example 3

Polymorph III

Method a: To a mixture of 5 mL of toluene and 1.5 mL of pyridine 0.5 g of N-(6-(4-chlorophenoxy)hexyl)-N'-cyano-N"-(4-pyridyl)guanidine was added. The resulting mixture was heated to 125° C. to obtain a clear solution. The resulting clear solution was stood and cooled to room temperature, moved into a refrigerator at 5° C. and refrigerated for 0.5 h, and then filtered under suction. The cake was dried in air to obtain the polymorph III. Melting Point: 146.8-148.5° C.

The X-ray powder diffraction pattern of the polymorph III was shown in FIG. 3.

Example 4

Polymorph IV

Method a: 0.5 g of N-(6-(4-chlorophenoxy)hexyl)-N'-cyano-N"-(4-pyridyl)guanidine was added to 3 mL of methanol. The resulting mixture was heated to 75° C. to obtain a clear solution. The resulting clear solution was stood and cooled to room temperature, moved into a refrigerator at 5° C. and refrigerated for 20 min, and then filtered under suction. The cake was dried in air to obtain the polymorph IV. Melting Point: 152.2-155° C.

Method b: 0.5 g of N-(6-(4-chlorophenoxy)hexyl)-N'-cyano-N"-(4-pyridyl)guanidine was added to 10 mL of absolute ethanol. The resulting mixture was heated to 85° C. to obtain a clear solution. The resulting clear solution was cooled to room temperature under stirring, and then filtered under suction. The cake was dried in air to obtain the polymorph IV.

The X-ray powder diffraction pattern of the polymorph IV was shown in FIG. 4.

Example 5

Polymorph V

Method a: 0.5 g of the polymorph VI of N-(6-(4-chlorophenoxy)hexyl)-N'-cyano-N"-(4-pyridyl)guanidine was added to 10 mL of ethyl acetate. The resulting mixture was heated to 80° C. and refluxed for 0.5 h, and did not form a clear solution. The resulting mixture was stood and cooled to room temperature, and then filtered under suction. The cake was dried in air to obtain the polymorph V. Melting Point: 144-146° C.

Method b: 0.5 g of the polymorph VI of N-(6-(4-chlorophenoxy)hexyl)-N'-cyano-N"-(4-pyridyl)guanidine was added to 18 mL of carbon tetrachloride. The resulting mixture was heated to 95° C. and stirred for 0.5 h, and did not form a clear solution. The resulting mixture was stood and cooled to room temperature, and then filtered under suction. The cake was dried in air to obtain the polymorph V.

The X-ray powder diffraction pattern of the polymorph V was shown in FIG. 5.

Example 6

Polymorph VI

To a mixture of 5 mL of DMSO (dimethylsulfoxide) and 2 mL of water 0.5 g of N-(6-(4-chlorophenoxy)hexyl)-N'-cyano-N"-(4-pyridyl)guanidine was added. The resulting mixture was heated to 95° C. to obtain a clear solution. The resulting clear solution was stood and cooled to room temperature, and then filtered under suction. The cake was washed with 4 mL of water once and dried in air to obtain the polymorph VI. Melting Point: 144.6-146.5° C.

The X-ray powder diffraction pattern of the polymorph VI was shown in FIG. 6.

According to FIGS. 1-6, the peaks with peak intensity equal or greater than 15 in X-ray powder diffraction patterns of the above-mentioned six polymorphs of N-(6-(4-chlorophenoxy)hexyl)-N'-cyano-N"-(4-pyridyl)guanidine or of the solvates thereof have the following features, respectively.

(1) Polymorph I of N-(6-(4-chlorophenoxy)hexyl)-N'-cyano-N"-(4-pyridyl)guanidine

| Diffraction angle (2θ, °) | Intensity (I/I$_0$) | Diffraction angle (2θ, °) | Intensity (I/I$_0$) |
|---|---|---|---|
| 15.679 | 15.3 | 15.940 | 16.5 |
| 17.901 | 100 | 18.779 | 20.4 |
| 21.439 | 46.4 | 25.781 | 36.6 |
| 26.162 | 16.6 | 26.861 | 32.5 |

(2) Polymorph II of N-(6-(4-chlorophenoxy)hexyl)-N'-cyano-N"-(4-pyridyl)guanidine

| Diffraction angle (2θ, °) | Intensity (I/I₀) | Diffraction angle (2θ, °) | Intensity (I/I₀) |
|---|---|---|---|
| 4.978 | 18.0 | 16.199 | 30.3 |
| 18.080 | 24.3 | 19.061 | 54.5 |
| 21.401 | 24.1 | 23.219 | 100.0 |
| 25.939 | 22.0 | | |

(3) Polymorph III of N-(6-(4-chlorophenoxy)hexyl)-N'-cyano-N"-(4-pyridyl)guanidine

| Diffraction angle (2θ, °) | Intensity (I/I₀) | Diffraction angle (2θ, °) | Intensity (I/I₀) |
|---|---|---|---|
| 5.378 | 100 | 10.741 | 60.3 |
| 16.140 | 93.5 | 20.939 | 16.4 |

(4) Polymorph IV of N-(6-(4-chlorophenoxy)hexyl)-N'-cyano-N"-(4-pyridyl)guanidine

| Diffraction angle (2θ, °) | Intensity (I/I₀) | Diffraction angle (2θ, °) | Intensity (I/I₀) |
|---|---|---|---|
| 14.340 | 26.5 | 15.821 | 16.3 |
| 16.759 | 15.9 | 18.040 | 100.0 |
| 20.201 | 50.1 | 20.921 | 34.3 |
| 21.421 | 57.3 | 23.781 | 58.7 |
| 24.139 | 16.6 | 24.660 | 57.9 |
| 26.260 | 16.1 | 26.484 | 20.2 |

(5) Polymorph V of N-(6-(4-chlorophenoxy)hexyl)-N'-cyano-N"-(4-pyridyl)guanidine

| Diffraction angle (2θ, °) | Intensity (I/I₀) | Diffraction angle (2θ, °) | Intensity (I/I₀) |
|---|---|---|---|
| 15.701 | 19.3 | 15.999 | 39.2 |
| 17.901 | 100 | 18.839 | 38.9 |
| 21.479 | 79.3 | 23.159 | 34.2 |
| 25.841 | 66.8 | 26.219 | 15.2 |
| 26.920 | 51.2 | | |

(6) Polymorph VI of N-(6-(4-chlorophenoxy)hexyl)-N'-cyano-N"-(4-pyridyl)guanidine

| Diffraction angle (2θ, °) | Intensity (I/I₀) | Diffraction angle (2θ, °) | Intensity (I/I₀) |
|---|---|---|---|
| 5.023 | 15.2 | 16.240 | 39.5 |
| 19.121 | 67.6 | 23.260 | 100 |
| 25.979 | 23.5 | | |

The above-mentioned six polymorphs of N-(6-(4-chlorophenoxy)hexyl)-N'-cyano-N"-(4-pyridyl)guanidine according to the present invention were exposed to the air at room temperature for 12 months, and then purities thereof were measured by using high performance liquid chromatography. The obtained purity results thereof were shown s follows.

| Polymorph | Original Purity (%) | Purity (after exposed for 12 months) (%) |
|---|---|---|
| Polymorph I | 98.01 | 97.49 |
| Polymorph II | 99.45 | 99.36 |
| Polymorph III | 97.83 | 97.56 |
| Polymorph IV | 99.59 | 99.45 |
| Polymorph V | 95.82 | 95.02 |
| Polymorph VI | 99.55 | 99.28 |

The purities were measured by using high performance liquid chromatography under the following conditions.

Chromatographic Column. PLATISIL ODS (150*4.6 mm, 5μ)

Mobile Phase:

Phase A: 11.5% (v/v) of acetonitrile aqueous solution containing 0.01 mol/L of lauryl sodium sulfate and 0.0125 mol/L of dipotassium hydrogen phosphate (adjusted to pH 2.5 with phosphoric acid)

Phase B: acetonitrile

| Linear Gradient Elution Table | | | |
|---|---|---|---|
| Time (minute) | Mobile phase A (%) | Mobile phase B (%) | Note |
| 0 | 60 | 40 | — |
| 4 | 50 | 50 | — |
| 8.8 | 50 | 50 | — |
| 12 | 34 | 66 | — |
| 25 | 34 | 66 | — |
| 25.01 | 60 | 40 | — |
| 35 | 60 | 40 | or operated f or 10 min later |

Column Temperature: 40° C.;
Detection Wavelength: 278 nm;
Flow Rate: 1 ml/min.

It can be seen from the above data that the purities of the above-mentioned six polymorphs of N-(6-(4-chlorophenoxy)hexyl)-N'-cyano-N"-(4-pyridyl)guanidine or of the solvates thereof according to the present invention did not change obviously after exposed to the air at room temperature for 12 months, and no significant degradation product was produced, which suggests that the polymorphs according to the present invention have highly excellent stability.

The invention claimed is:

1. A polymorph of N-(6-(4-chlorophenoxy)hexyl)-N'-cyano-N"-(4-pyridyl)guanidine, characterized in that the X-ray powder diffraction pattern of the polymorph of N-(6-(4-chlorophenoxy)hexyl)-N'-cyano-N"-(4-pyridyl)guanidine has the following peaks:

| Diffraction angles (2θ, °) | Intensity (I/I₀) | Diffraction angles (2θ, °) | Intensity (I/I₀) |
|---|---|---|---|
| 14.340 | 26.5 | 15.821 | 16.3 |
| 16.759 | 15.9 | 18.040 | 100.0 |
| 20.201 | 50.1 | 20.921 | 34.3 |
| 21.421 | 57.3 | 23.781 | 58.7 |
| 24.139 | 16.6 | 24.660 | 57.9 |
| 26.260 | 16.1 | 26.484 | 20.2. |

2. The polymorph of of claim 1, wherein a unit dosage of the polymorph when used as an active ingredient is in the range of 0.1 mg to 500 mg.

3. A formulation comprising the polymorph of claim 1, wherein the formulation is a tablet, a capsule, a conventional powder for injection, a lyophilized powder for injection, a patch or an implant, which can be used via injection, oral, inhalation, transdermal, rectal or vaginal administration.

* * * * *